US00PP36497P2

(12) United States Plant Patent
Horvath

(10) Patent No.: US PP36,497 P2
(45) Date of Patent: Feb. 25, 2025

(54) ***SANGUISORBA* PLANT NAMED 'Plum Drops'**

(50) Latin Name: ***Sanguisorba* hybrid**
Varietal Denomination: Plum Drops

(71) Applicant: Brent Arpad Horvath, Hebron, IL (US)

(72) Inventor: Brent Arpad Horvath, Hebron, IL (US)

( * ) Notice: Subject to any disclaimer, the term of this patent is extended or adjusted under 35 U.S.C. 154(b) by 0 days.

(21) Appl. No.: 18/445,738

(22) Filed: Jan. 10, 2024

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05)

(58) Field of Classification Search
USPC ..... Plt./263.1
CPC ..... A01H 6/74; A01H 5/02
See application file for complete search history.

*Primary Examiner* — Keith O. Robinson

(57) ABSTRACT

A new, distinct *Sanguisorba* plant named 'Plum Drops' as illustrated and described, characterized by the combination of dark green pinnate foliage and intermediate size, growing 110 cm in height and large dark red flowers.

1 Drawing Sheet

Figure 1:
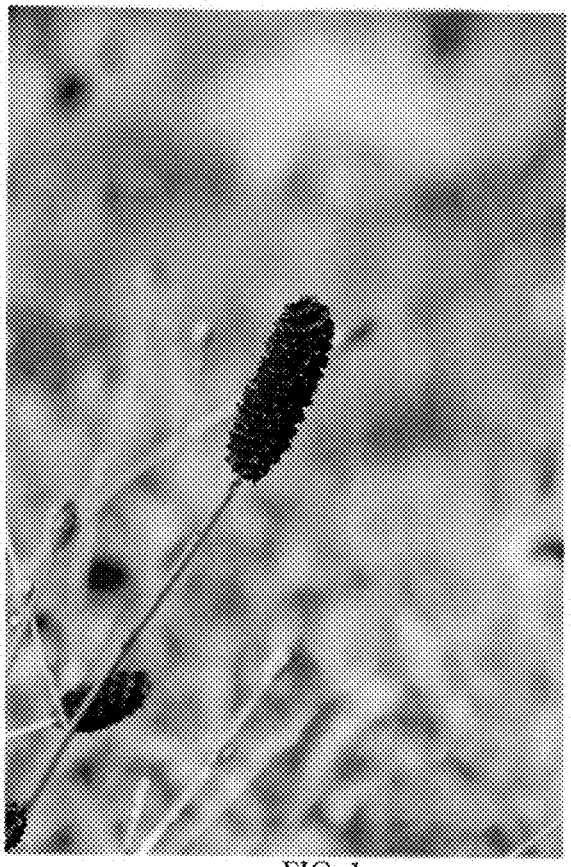

Latin name: *Sanguisorba* hybrid.
Cultivar name: 'Plum Drops'.

BACKGROUND OF THE INVENTION

The present invention relates to a new and distinct hybrid of *Sanguisorba* plant named 'Plum Drops' characterized by the combination of dark green pinnate foliage and intermediate size, growing 110 cm in height and large dark red flowers. The new *Sanguisorba* was raised as a seedling from open pollinated seed sown from the seed parent *Sanguisorba officinalis* 'Tanna', not patented, in Hebron, IL in 2019. The selection of the new plant was due to its' larger dark green foliage, taller stems, larger dark red flowers, compared to the seed parent. Initial asexual reproduction has taken place at a nursery in Hebron, IL since 2022 by means of vegetative division. The new *Sanguisorba* has shown to be stable and identical in reproduction to the initially discovered plant after rooting over 400 plants from 2020 to 2022. No plants of the new *Sanguisorba* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor. Actual first date of sale was Apr. 20, 2023.

SUMMARY OF THE INVENTION

The new *Sanguisorba* plant named 'Plum Drops' characterized by dark green pinnate foliage and intermediate size, growing 110 cm in height and large dark red flowers have been observed to be unique and stable.

Plants of the new *Sanguisorba* plant named 'Plum Drops' can be compared to the seed parent plant of *Sanguisorba officinalis* 'Tanna', not patented. 1. The 'Plum Drops' plant is taller growing to 110 cm while *Sanguisorba officinalis* 'Tanna' grows to 60 cm. 2. The 'Plum Drops' plant has larger foliage up to 35 cm in length while *Sanguisorba officinalis* 'Tanna' foliage grows to 15 cm in length. 3. The 'Plum Drops' plant has a larger flower, 3-4 cm in length while *Sanguisorba officinalis* 'Tanna' has flower size of 2 cm in length.

Plants of the new *Sanguisorba* plant named 'Plum Drops' can also be compared to the pollen parent plant of *Sanguisorba tenuifolia* 'Purpurea', not patented. 1. The 'Plum Drops' plant is shorter growing to 110 cm while *Sanguisorba tenuifolia* 'Purpurea' grows to 150 cm. 2. The 'Plum Drops' plant has smaller foliage up to 35 cm in length while *Sanguisorba tenuifolia* 'Purpurea' foliage grows to 45 cm in length. 3. The 'Plum Drops' plant has a smaller flower, 3-4 cm in length while *Sanguisorba tenuifolia* 'Purpurea' has flower size of 6 cm in length.

Plants of the new *Sanguisorba* plant named 'Plum Drops' can also be compared to plants of *Sanguisorba* 'Red Dream', U.S. Plant Pat. No. 32,441. 1. The 'Plum Drops' plant is shorter growing to 110 cm while *Sanguisorba* 'Red Dream' grows to 120 cm or more. 2. The 'Plum Drops' plant has larger foliage up to 35 cm in length while *Sanguisorba* 'Red Dream' foliage grows to 19 cm in length. 3. The 'Plum Drops' plant has a larger flowers, 3-4 cm in length while *Sanguisorba* 'Red Dream' has flower size of 3 cm in length.

DESCRIPTION OF PHOTOGRAPHS

Figure 2:
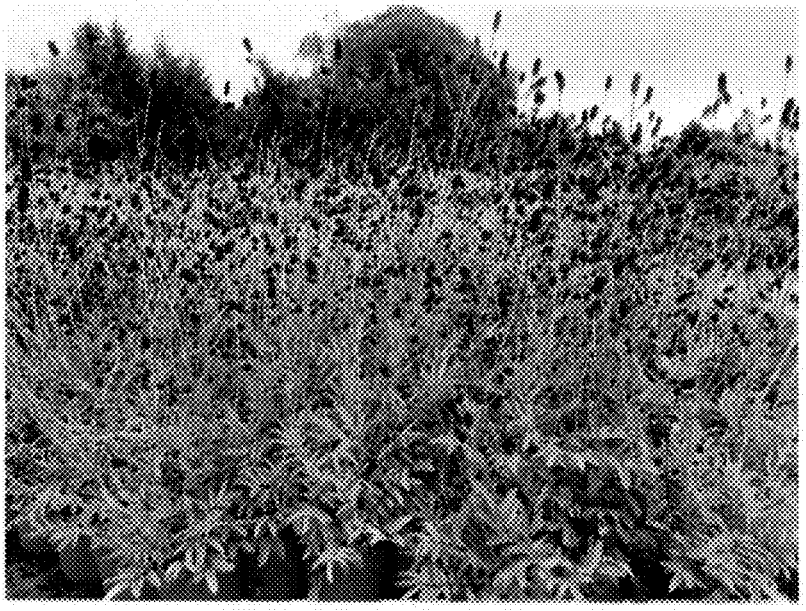

Plants pictured in the drawing were grown for one year.
FIG. 1. Close up of the flower.
FIG. 2. A group of blooming plants.

DETAILED BOTANICAL DESCRIPTION

In the following description, color references are made to The Royal Horticultural Society Colour Chart (2001). Plants used for the description were grown for two years. Measurements and numerical values represent averages of typical plants.

Plant description:

*Botanical classification.*—*Sanguisorba* plant named 'Plum Drops'.

*Form*.—Upright, mounded. Flower stems arise from the roots; Moderate branching, with numerous crowded flower spikes starting in Mid-July and continuing through August.

*Parentage*.—Female, or seed, parent. — *Sanguisorba officinalis* 'Tanna'; Male, or pollen, parent. — *Sanguisorba tenuifolia* 'Purpurea'.

*Propagation*.—Type: division and tissue culture.

*Height*.—110 cm from soil to top of flowers; Width: 70 cm.

*Growth*.—Herbaceous perennial, broad upright, vigorous.

*Roots*.—Moderate, fibrous, freely branching, brown 199 C.

Stem:

*Form*.—Rounded, strong. Aspect — 10 degrees to vertical.

*Stem color*.—Both young and old 146 D.

*Texture*.—Smooth glabrous.

*Branching*.—Moderate branching from the stem, typically 8 lateral branches, no pinching required.

*Diameter*.—5 mm. Length. — 110 cm. Internode length — 10 cm.

*Quantity*.—Up to 10 flowering branches, 10 cm in length.

Foliage:

*Arrangement*.—Alternate, pinnate. Aspect — 25 degrees.

*Size of leaf*.—Length: 36 cm on average including petiole, shorter at tops of stems.

*Width*.—10 cm.

*Shape of leaf*.—Lanceolate. Shape of tip. — Acute. Shape of base. — truncate.

*Texture*.—Smooth, glabrous. Margin type. — Dentate.

*Color*.—Young and Mature leaves: Upper surface: 137 A. Lower surface: 146 B.

*Leaflet*.—Oblong in shape, 4-5 cm in length, 2 cm in width. Upper color 137 B, lower color 146 B.

*Leaflet venation*.—Pinnate, upper and lower surface conspicuous. Upper color 137 B, lower color 146 B. Margins — Crenate. Surface — both surfaces smooth, glabrous.

*Petioles*.—Length: 35 cm on average for lower leaves; 3 mm width. Diameter — 1-1.5 mm.

*Stipules*.—At the base of each leaf is a leafy stipule on each side, falcate in shape, 4 mm in length, 2 mm in width. Surface is smooth and glabrous, crenate margins, color of upper surface 137 B, color of the lower surface 146 B.

*Veins*.—Pattern: Pinnate. Color: Upper surface: 137 B. Lower surface: 146 B.

*Leaf durability*.—Highly durable to stresses.

*Response time to flower*.—About 3 months when grown in the containers.

Flower description:

*Flower type*.—Terminal spikes of numerous, densely packed flowers in elongated ovoid to oblong shaped inflorescence, determinate.

*Natural flowering season*.—from Mid-July through August.

*Inflorescence type and habit*.—Terminal spikes, densely packed in elongated oblong shape.

*Rate of flower opening*.—About 10% of flowers open at once, all flowers open in about 6weeks.

*Number of flowers*.—About 170 per spike; about 1000 flowers per lateral branch.

*Bud texture*.—Smooth, glabrous, and matte surface, Shape. — Orbicular.

*Length*.—2 mm. Diameter — 2 mm. Color — N77 A. Inflorescence size: Diameter — 2 cm.

*Height*.—4 cm. 1 cm in depth.

*Response time to flower*.—About 2 months when grown in the containers.

Peduncle:

*Length*.—12 cm. Diameter — 2 mm. Color — 145 A.

*Texture*.—Smooth. Strength — Strong.

*Texture*.—Upper and lower surfaces: smooth glabrous. Aspect — Rotate, single, outward and freely flowering.

*Petals*.—Rotate, cruciform, average of 4, 1 row, unfused, 3 mm in length, 2 mm in width, ovate in shape, acute tip, cuneate base, entire margins, both surfaces glabrous, slightly velvety and matte, color; when opening upper and lower surface N79 A, and base 145 D, when fully open upper surface N77 A with base 150 D.

*Calyx*.—Rotate, cruciform, average of 3 mm in length and diameter.

*Sepals*.—Number — An average of 4 in 1 row.

*Shape*.—Ovate, acute tip, cuneate base, entire margins. Size: Average 2 mm long; 1 mm or less wide. Margin: Entire. Texture — both surfaces matte and moderately pubescent with short adpressed hairs; average of 0.3 mm in length and too small to measure color.

*Color*.—When opening upper and lower surface N79 C, fully open upper and lower surface N199 D with apex N199 C. Bract tissue; 7 mm long, 2 mm wide; Color at base N77 A and tip 79 A.

Reproductive organs:

*Androecium*.—Stamens; average of 4, filament; 2 mm in length, N155 D in color, anthers; broad oblong in shape, 0.3 mm in length, 0.2 mm in width, pollen; low in quantity, 11 B in color.

*Gynoecium*.—Pistil: 1, average of 1.5 mm in length, stigma is flattened and club-shaped, 5 mm in length and diameter, 59 A in color, style; average of 1.25 mm in length, 59 C in color, ovary; 145 C in color.

*Seeds and fruits*.—Brown and round 1 mm long and 1 mm wide, color 200 B. Fragrance. — Faint and unpleasant.

*Flower lastingness*.—About 14 days, persistent.

*Disease/pest resistance*.—No unusual susceptibility to diseases or pests has been noted to date. Temperature tolerance: Tolerate to heat at least up to 30° C. and cool at least down to USDA Zone 5.

I claim:

1. A new and distinct *Sanguisorba* plant named 'Plum Drops' as illustrated and described herein.

* * * * *